US007803567B2

(12) United States Patent
Alderete et al.

(10) Patent No.: US 7,803,567 B2
(45) Date of Patent: Sep. 28, 2010

(54) METHODS AND COMPOSITIONS FOR DETECTING *TRICHOMONAS* IN A SAMPLE CONTACTED WITH FIXATIVE

(75) Inventors: John F. Alderete, San Antonio, TX (US); Te-Hung Chang, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 93 days.

(21) Appl. No.: 11/634,766

(22) Filed: Dec. 6, 2006

(65) Prior Publication Data

US 2007/0134741 A1 Jun. 14, 2007

Related U.S. Application Data

(60) Provisional application No. 60/749,153, filed on Dec. 9, 2005.

(51) Int. Cl.
G01N 33/571 (2006.01)

(52) U.S. Cl. .................. 435/7.36; 435/40.5; 435/40.51

(58) Field of Classification Search ........................ None
See application file for complete search history.

(56) References Cited

U.S. PATENT DOCUMENTS

| | | | |
|---|---|---|---|
| 4,514,498 A | 4/1985 | Kettman et al. | |
| 4,707,442 A | 11/1987 | Alderete | |
| 4,861,711 A | 8/1989 | Friesen et al. | |
| 5,004,694 A | 4/1991 | Moay et al. | |
| 5,037,615 A | 8/1991 | Kane | |
| 5,256,571 A * | 10/1993 | Hurley et al. | 436/17 |
| 5,330,897 A | 7/1994 | Pindak et al. | |
| 5,369,005 A | 11/1994 | Baseman et al. | |
| 5,415,994 A | 5/1995 | Imrich et al. | |
| 5,516,638 A | 5/1996 | Umovitz et al. | |
| 5,679,551 A | 10/1997 | Alderete | |
| 5,741,662 A | 4/1998 | Madsen et al. | |
| 5,776,694 A | 7/1998 | Sheiness et al. | |
| 5,876,985 A | 3/1999 | Alderete | |
| 5,879,881 A | 3/1999 | Rubenstein | |
| 5,922,563 A | 7/1999 | Alderete | |
| 6,063,905 A | 5/2000 | Capra et al. | |
| 6,174,293 B1 | 1/2001 | Buck et al. | |
| 6,207,395 B1 | 3/2001 | Valkirs et al. | |
| 6,528,321 B1 | 3/2003 | Fitzgerald et al. | |
| 6,824,975 B2 | 11/2004 | Hubscher et al. | |
| 7,291,477 B2 | 11/2007 | Alderete et al. | |
| 2002/0045195 A1 | 4/2002 | Hubscher et al. | |
| 2003/0032029 A1 | 2/2003 | Collins | |
| 2003/0073147 A1 | 4/2003 | Alderete | |
| 2004/0072280 A1 | 4/2004 | Lawrence et al. | |
| 2007/0009974 A1 | 1/2007 | Alderete et al. | |
| 2007/0015224 A1 | 1/2007 | Alderete et al. | |
| 2007/0077606 A1 | 4/2007 | Alderete et al. | |
| 2007/0134741 A1 | 6/2007 | Alderete et al. | |

FOREIGN PATENT DOCUMENTS

| | | |
|---|---|---|
| EP | 0 050 424 B1 | 4/1982 |
| EP | 0 810 436 A1 | 12/1997 |
| WO | WO 92/07096 A1 | 4/1992 |

OTHER PUBLICATIONS

Batista et al (Cell Structure and Function, 13:445-453, 1988).*
Xingze et al, (Chinese Journal of Parisitology and Parasitic Diseases 13(1):68-70, 1995).*
Burgess et al, (J. Parasitiology, 75(6):977-980, 1989).*
Schwebke et al (Clinical Microbiology Reviews, 17(4):794-803, Oct. 2004).*
Addis et al (The Journal of Infectious Diseases, 180:1727-30, 1999).*
PTO Translation of Xingze et al (PTO 08/7994).*
Addis et al, Infection and Immunity 66(10):4924-4931, 1998.*
Weise et al (American Journal of Medicine, 108:301-308, 2000).*
Addis et al. "Cloning and Molecular Characterization of a cDNA Clone Coding for *Trichomonas vaginalis* Alpha-Actinin and Intracellular Localization of the Protein" *Infection and Immunity* 66(10):4924-4931 (1998).
Addis et al. "Host and Tissue Specificity of *Trichomonas vaginalis* is Not Mediated by its Known Adhesion Proteins" *Infection and Immunity* 68(7):4358-4360 (2000).
Alderete. "Identification of Immunogenic and Antibody-Binding Membrane Proteins of Pathogenic *Trichomonas vaginalis*" *Infection and Immunity* 40(1):284-291 (1983).
Alderete and Garza "Identification and Properties of *Trichomonas vaginalis* Proteins Involved in Cytadherence" *Infection and Immunity* 56(1):28-33 (1988).
Alderete and Garza "Soluble *Trichomonas vaginalis* Antigens in Cell-Free Culture Supernatants" *Molecular and Biochemical Parasitology* 13:147-158 (1984).
Alderete and Kasmala "Monoclonal Antibody to a Major Glycoprotein Immunogen Mediates Differential Complement-Independent Lysis of *Trichomonas vaginalis*" *Infection and Immunity* 53(3):697-699 (1986).
Alderete et al. "Cloning and Molecular Characterization of Two Genes Encoding Adhesion Proteins Involved in *Trichomonas vaginalis* Cytoadherence" *Molecular Microbiology* 17(1):69-83 (1995).
Alderete et al. "Heterogeneity of *Trichomonas vaginalis* and Discrimination among Trichomonal Isolates and Subpopulations with Sera of Patients and Experimentally Infected Mice" *Infection and Immunology* 49(3):463-468 (1985).
Alderete et al. "Monoclonal Antibody to a Major Surface Glycoprotein Immunogen Differentiates Isolates and Subpopulations of *Trichomonas vaginalis*" *Infection and Immunity* 52(1):70-75 (1986).

(Continued)

*Primary Examiner*—Patricia A Duffy
(74) *Attorney, Agent, or Firm*—Myers Bigel Sibley & Sajovec, P.A.

(57) ABSTRACT

The present invention provides methods and compositions for detecting a *Trichomonas* antigen in a fixed sample and for diagnosing *Trichomonas* infection by detecting a *Trichomonas* antigen in a fixed sample.

12 Claims, No Drawings

OTHER PUBLICATIONS

Alderete et al. "Only Two of the *Trichomonas vaginalis* Triplet AP51 Adhesins Are Regulated by Iron" *Microbial Pathogenesis* 24:1-16 (1998).

Alderete et al. "Phenotypes and Protein-Epitope Phenotypic Variation Among Fresh Isolates of *Trichomonas vaginalis*" *Infection and Immunity* 55(5):1037-1041 (1987).

Alderete et al. "Phenotypic Variation and Diversity Among *Trichomonas vaginalis* Isolates and Correlation of Phenotype with Trichomonal Virulence Determinants" *Infection and Immunity* 53(2):285-293 (1986).

Alderete et al. "Specific Parasitism of Purified Vaginal Epithelial Cells by *Trichomonas vaginalis*" *Infection and Immunity* 56(10):2558-2562 (1988).

Alderete et al. "*Trichomonas vaginalis* Genetic Analysis of Cell Adherence" Abstract from CRISP website for Grant No. 2R21AI043940-05, Fiscal Year 2003.

Alonzo and Pepe "Using a Combination of Reference Tests to Assess the Accuracy of a New Diagnostic Test" *Statistics in Medicine* 18:2987-3003 (1999).

Arroyo et al. "Characterization of cDNAs Encoding Adhesin Proteins Involved in *Trichomonas vaginalis* Cytoadherence" *Archives of Medical Research* 26(4):361-369 (1995).

Arroyo et al. "Molecular Basis of Host Epithelial Cell Recognition by *Trichomonas vaginalis*" *Molecular Microbiology* 6(7):853-862 (1992).

Arroyo et al. "Signalling of *Trichomonas vaginalis* for Amoeboid Transformation and Adhesin Synthesis Follows Cytoadherence" *Molecular Microbiology* 7(2):299-309 (1993).

Baseman et al. "San Antonio STI TM CRC" Abstract from the CRISP website for Grant No. 2U19AI045429-06, Fiscal Year 2004.

Benchimol et al. "Structure and Division of the Golgi Complex in *Trichomonas vaginalis* and *Tritrichomonas foetus*" *European Journal of Cell Biology* 80:593-607 (2001).

Bricheux et al. "Evidence for an Uncommon α-actinin Protein in *Trichomonas vaginalis*" *Molecular and Biochemical Parasitology* 95:241-249 (1998).

Checkoway et al. "Medical, Life-Style, and Occupational Risk Factors for Prostate Cancer" *The Prostate* 10:79-88 (1987).

Cogne et al. "Detection and Characterization of Serum Antitrichomonal Antibodies in Urogenital Trichomoniasis" *Journal of Clinical Microbiology* 21(4):588-592 (1985).

Cuatrecasas "Protein Purification by Affinity Chromatography" *The Journal of Biological Chemistry* 245(12):3059-3065 (1970).

Dalchau et al. "Monoclonal Antibody to a Human Leukocyte-Specific Membrane Glycoprotein Probably Homologous to the Leukocyte-Common (L-C) Antigen of the Rat" *Eur. J. Immunol.* 10:737-744 (1980).

Dennis et al. "Meta-Analysis of Measures of Sexual Activity and Prostate Cancer" *Epidemiology* 13(1):72-79 (2002).

Engbring et al. "Characterization of *Trichomonas vaginalis* AP33 Adhesin and Cell Surface Interactive Domains" *Microbiology* 144:3011-3018 (1998).

Engbring et al. "Three Genes Encode Distinct AP33 Proteins Involved in *Trichomonas vaginalis* Cytoadherence" *Molecular Microbiology* 28(2):305-313 (1998).

Estrada et al. "Reporting and Concordance of Methodologic Criteria Between Abstracts and Articles in Diagnostic Test Studies" *JGIM* 15:183-187 (2000).

European Search Report for EP 03746064.9 Dated Mar. 22, 2007.

Garber et al. "Cell Culture Compared with Broth for Detection of *Trichomonas vaginalis*" *Journal of Clinical Microbiology* 25(7):1275-1279 (1987).

Garber et al. "Immunogenic Proteins of *Trichomonas vaginalis* as Demonstrated by the Immunoblot Technique" *Infection and Immunity* 51(1):250-253 (1986).

Genzyme Diagnostics Product Information Sheet for OSOM *Trichomonas* Rapid Test. Printed from Genzyme website (2 pages)(Apr. 2007).

Hobbs et al. "Methods for Detection of *Trichomonas vaginalis* in the Male Partners of Infected Women: Implications for Control of Trichomoniasis" *Journal of Clinical Microbiology* 44(11):3994-3999 (2006).

Huppert et al. "Use of an Immunochromatographic Assay for Rapid Detection of *Trichomonas vaginalis* in Vaginal Specimens" *J. Clin. Microbiol.* 43(2):684-687 (2005).

Huse et al. "Generation of a Large Combinatorial Library of the Immunoglobulin Repertoire in Phage Lambda" *Science* 246:1275-1281 (1989).

International Search Report corresponding to International Application No. PCT/US03/09474, mailed Jul. 21, 2003.

Köhler and Milstein "Continuous Cultures of Fused Cells Secreting Antibody of Predefined Specificity" *Nature* 256:495-497 (1975).

Krieger et al. "Clinical Manifestations of Trichomoniasis in Men" *Annals of Internal Medicine* 118(11):844-849 (1993).

Kuberski. "Ankylosing Spondylitis Associated with *Trichomonas vaginalis* Infection" *Journal of Clinical Microbiology* 13(5):880-881 (1981).

Kucknoor et al. "Adherence to Human Vaginal Epithelial Cells Signals for Increased Expression of *Trichomonas vaginalis* Genes" *Infection and Immunity* 73(10):6472-6478 (2005).

Lehker and Sweeney "Trichomonad Invasion of the Mucous Layer Requires Adhesins, Mucinases, and Motility" *Sex. Transm. Inf.* 75:231-238 (1999).

Lehker et al. "The Regulation by Iron of the Synthesis of Adhesins and Cytoadherence Levels in the Protozoan *Trichomonas vaginalis*" *J. Exp. Med.* 174:311-318 (1991).

Lisi et al. "Monoclonal-Antibody-Based Enzyme-Linked Immunosorbent Assay for *Trichomonas vaginalis*" *Journal of Clinical Microbiology* 26(9):1684-1686 (1988).

Mathews et al. "Evaluation of Two Serological Tests for *Trichomonas vaginalis* Infection" *Journal of Clinical Microbiology* 17(5):840-843 (1983).

Miller et al. "Assessment of a Rapid Antigen Detection System for *Trichomonas vaginalis* Infection" *Clinical and Diagnostic Laboratory Immunology* 10(6):1157-1158 (2003).

Mohamed et al. "Urine Proves a Poor Specimen for Culture of *Trichomonas vaginalis* in Women" *Sex. Transm. Infect.* 77(1):78-79 (2001).

O'Brien et al. "Molecular Characterization of a Third Malic Enzyme-Like AP65 Adhesin Gene of *Trichomonas vaginalis*" *Microbial Pathogenesis* 20:335-349 (1996).

Patel et al. "Systematic Review of Diagnostic Tests for Vaginal Trichomoniasis" *Infectious Diseases in Obstetrics and Gynecology* 8:248-257 (2000).

Planned Parenthood Report "XenoStrip™—Tv *Trichomonas* Test Clinical Efficacy Assessment" Xenotope Diagnostices, Inc. (22 pages)(Jan. 22, 2004).

Ponce de Leon et al. "Relation Between Buccal Protozoa and pH and Salivary IgA in Patients with Dental Prothesis" *Rev. Inst. Med. Trop. S Paulo* 43:4 (4 pages) (2001).

Rappelli et al. "Sequence of cDNA coding for a 65 kDa Adhesive Protein for the Specific Detection of *Trichomonas vaginalis* by PCR" *FEMS Microbiology Letters* 129:21-26 (1995).

Rosenblatt et al. "Sexual Factors and the Risk of Prostate Cancer" *American Journal of Epidemiology* 153(12):1152-1158 (2001).

Stary et al. "Detection of *Trichomonas vaginalis* on Modified Columbia Agar in the Routine Laboratory" *Journal of Clinical Microbiology* 40(9):3277-3280 (2002).

Sutcliffe et al. "Plasma Antibodies Against *Chlamydia trachomatis*, Human Papillomavirus, and Human Herpesvirus Type 8 in Relation to Prostate Cancer: a Prospective Study" *Cancer Epidemiol Biomarkers Prev.* 16(8):1573-1580 (2007).

Sutcliffe et al. "Plasma Antibodies Against *Trichomonas vaginalis* and Subsequent Risk of Prostate Cancer" Abstract of poster presented at the 4th Annual American Association for Cancer Research International Conference entitled "Frontiers in Cancer Prevention Research." Baltimore, MD (3 pages)(Oct. 30, 2005-Nov. 2, 2005).

Sutcliffe et al. "Plasma Antibodies Against *Trichomonas vaginalis* and Subsequent Risk of Prostate Cancer" *Cancer Epidemiol Biomarkers Prev.* 15(5):939-945 (2006).

Van der Schee et al. "Improved Diagnosis of *iTrichomonas vaginalis* Infection by PCR Using Vaginal Swabs and Urine Specimens Compared to Diagnosis by Wet Mount Microscopy, Culture, and Flourescent Staining" *Journal of Clinical Microbiology* 37(12):4127-4130 (1999).

Wasserheit. "Epidemiological Synergy: Interrelationships Between Human Immunodeficiency Virus Infection and Other Sexually Transmitted Diseases" *J. Sex. Trans. Dis.* 19(2):61-77 (1992).

Watson-Jones et al. "High Prevalence of Trichomoniasis in Rural Men in Mwanza, Tanzania: Results from a Population Based Study" *Sex. Transm. Inf.* 76:355-362 (2000).

Watt et al. "Rapid Assay for Immunological Detection of *Trichomonas vaginalis*" *Journal of Clinical Microbiology* 24(4):551-555 (1986).

Wiese et al. "A Meta-Analysis of the Papanicolaou Smear and Wet Mount for the Diagnosis of Vaginal Trichomoniasis" *The American Journal of Medicine* 108(4):301-308 (1999).

Wos et al. "Immunoglobulin Isotypes of Anti-*Trichomonas vaginalis* Antibodies in Patients with Vaginal Trichomoniasis" *Journal of Clinical Microbiology* 24(5):790-795 (1986).

Yap et al. "Serum Antibodies to *Trichomonas vaginalis* in Invasive Cervical Cancer Patients" *Genitourin Med.* 71:402-404 (1995).

Zhang et al. "*Trichomonas vaginalis* and Cervical Cancer: a Prospective Study in China" *AEP.* 5(4):325-332 (1995).

\* cited by examiner

METHODS AND COMPOSITIONS FOR DETECTING *TRICHOMONAS* IN A SAMPLE CONTACTED WITH FIXATIVE

STATEMENT OF PRIORITY

This application claims priority, under 35 U.S.C. §119(e), to U.S. Provisional Application No. 60/749,153, filed Dec. 9, 2005, the entire contents of which are incorporated by reference herein.

BACKGROUND OF THE INVENTION

*Trichomonas vaginalis* causes vaginitis in women and non-gonococcal non-chlamydial urethritis in men. An estimated 9 million new cases of trichomonosis occur each year in the US, the majority in women. This sexually transmitted infection (STI), called trichomonosis or trichomoniasis, is associated with adverse outcomes in pregnancy. In addition, this STI is associated with cervical cancer independent of human papilloma virus (HPV). Significantly, African Americans have the highest rates of trichomonosis in comparison with other American communities, and this STI contributes to the spread of HIV among women and minorities in the United States. Epidemiologic studies suggest that *Trichomonas vaginalis* is associated with a 2- to 4-fold increased risk of HIV transmission, contributing to health disparities. Therefore, control of trichomonosis through diagnosis and treatment may be one of the most effective means of reducing HIV.

The present invention overcomes previous shortcomings in the art by providing methods and compositions for diagnosing *Trichomonas* infection in a subject by detecting *Trichomonas* antigens in a biological sample that has been contacted with a fixative.

SUMMARY OF THE INVENTION

Thus, the present invention provides a method of detecting a *Trichomonas* antigen in a sample that has been contacted with fixative, comprising: a) contacting the sample with an antibody that specifically binds a fixed *Trichomonas* antigen under conditions whereby an antigen/antibody complex can form; and b) detecting the formation of an antigen/antibody complex, thereby detecting the *Trichomonas* antigen in the sample.

Also provided herein is a method of detecting a *Trichomonas* antigen in a sample, comprising: a) contacting the sample with a fixative; b) contacting the sample of (a) with an antibody that specifically binds a fixed *Trichomonas* antigen under conditions whereby an antigen/antibody complex can form; and c) detecting the formation of an antigen/antibody complex, thereby detecting the *Trichomonas* antigen in the sample.

The present invention further provides a method of diagnosing *Trichomonas* (e.g., *T. vaginalis*) infection in a subject, comprising: a) contacting a fixed sample from the subject with an antibody that specifically binds a fixed *Trichomonas* antigen under conditions whereby an antigen/antibody complex can form; and b) detecting formation of an antigen/antibody complex, thereby diagnosing a *Trichomonas* infection in the subject.

Additionally provided is a method of diagnosing *Trichomonas* infection in a subject, comprising: a) contacting a sample from the subject with a fixative; b) contacting the sample of (a) with an antibody that specifically binds a fixed *Trichomonas* antigen under conditions whereby an antigen/ antibody complex can form; and c) detecting formation of an antigen/antibody complex, thereby diagnosing *Trichomonas* infection in the subject.

DETAILED DESCRIPTION OF THE INVENTION

As used herein, "a" or "an" or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "*Trichomonas*" as used herein, includes, but is not limited to a protozoan parasite of the order *Trichomonadida*, genera *Ditrichonionas, Trichomonas, Tritrichomonas* and *Pentatrichomonas*, comprising multiple species that infects both humans and animals. "*Trichomonas*" refers to any *Trichomonas* species, e.g., *Tritrichomonas foetus* (also known as *Trichomonas foetus, Tt. fetus*), *Tt enteris* and *T. paviovi*, which infect cattle; *Tt. suis, Tt. rotunda* and *T. buttreyi*, which infect swine; *Dt. Ovis*, which infects sheep; *Tt. equi* and *T. equibuccalis*, which infect horses; *T. anatis, Tt. eberthi, T. gallinae* and *T. gallinarum*, which infect birds; *Tt. caviae, Tt. muris, Tt. wenoni, Tt. Minuta* and *T. microti*, which infect rodents; *T. canistomae* and *T. felistomae*, which infect dogs and cats; and *T. tenax, T. vaginalis, Pt. hominis*, and *T. macacovaginae*, which infect primates (including humans). *Trichomonas vaginalis* as described herein includes isolate T016 (Type I) and isolate T068 (Type II), as well as any other *T. vaginalis* isolate now known or later identified.

The present invention is based on the unexpected discovery that *Trichomonas* (e.g., *Trichomonas vaginalis*) antigens can be detected in a sample that has been contacted with a fixative and that infection with *Trichomonas* (e.g., *Trichomonas vaginalis*) can be diagnosed in a subject by detecting *Trichomonas* (e.g., *Trichomonas vaginalis*) antigens in a fixed biological sample from the subject.

Thus, the present invention provides a method of detecting a *Trichomonas* antigen in a sample that has been contacted with fixative, comprising: a) contacting the sample with an antibody that specifically binds a fixed *Trichomonas* antigen under conditions whereby an antigen/antibody complex can form; and b) detecting the formation of an antigen/antibody complex, thereby detecting the *Trichomonas* antigen in the sample.

Also provided herein is a method of detecting a *Trichomonas* antigen in a sample, comprising: a) contacting the sample with a fixative; b) contacting the sample of (a) with an antibody that specifically binds a fixed *Trichomonas* antigen under conditions whereby an antigen/antibody complex can form; and c) detecting the formation of an antigen/antibody complex, thereby detecting the *Trichomonas* antigen in the sample.

The present invention further provides a method of diagnosing *Trichomonas* (e.g., *T. vaginalis*) infection in a subject, comprising: a) contacting a fixed sample from the subject with an antibody that specifically binds a fixed *Trichomonas* antigen under conditions whereby an antigen/antibody complex can form; and b) detecting formation of an antigen/ antibody complex, thereby diagnosing a *Trichomonas* infection in the subject.

Additionally provided is a method of diagnosing *Trichomonas* infection in a subject, comprising: a) contacting a sample from the subject with a fixative; b) contacting the sample of (a) with an antibody that specifically binds a fixed *Trichomonas* antigen under conditions whereby an antigen/antibody complex can form; and c) detecting formation of an antigen/antibody complex, thereby diagnosing *Trichomonas* infection in the subject.

The present invention further provides a method of detecting an antibody that binds a *Trichomonas* antigen in a sample from a subject, comprising: a) contacting the sample from the subject with a fixed *Trichomonas* antigen under conditions whereby an antigen/antibody complex can form; and b) detecting formation of an antigen/antibody complex, thereby detecting the antibody.

Also provided herein is a method of diagnosing *Trichomonas* infection in a subject, comprising a) contacting a sample from the subject with a fixed *Trichomonas* antigen under conditions whereby an antigen/antibody complex can form; and b) detecting formation of the an antigen/antibody complex, thereby diagnosing *Trichomonas* infection in the subject.

In the methods of this invention, the sample can be any biological fluid, cell or tissue that can be used in an immunoassay of this invention, including but not limited to, serum, plasma, blood, saliva, semen, cerebrospinal fluid, prostatic fluid, urine, sputum, joint fluid, body cavity fluid, whole cells, cell extracts, tissue, biopsy material, aspirates, exudates, vaginal washings, vaginal and/or endocervical material and/or secretions (e.g., swabs), pap smear samples, pap smear preparations, slide preparations, tissue sections, etc., wherein the sample is contacted with fixative prior to contact with an antibody of this invention. The sample of this invention can be one or more of the samples described herein, individually and/or in any combination. In some embodiments involving methods of identifying antibodies of this invention as specifically binding a fixed *Trichomonas* antigen, the sample or source of the antigen can be any sample of this invention and/or can also be *Trichomonas* cells from a *T. vaginalis* culture (e.g., T016).

A fixative of this invention can be any substance or material that "fixes" (e.g., preserves or stabilizes) the material in the sample. As used herein, the terms "fix," "fixes," "fixing," etc., mean to preserve, stabilize or hold biological material in a configuration that is permanent, firmly in position and/or stable. Thus for example, a "fixed" antigen can be an antigen that is preserved in a permanent and stable configuration. In some embodiments, a "fixed" antigen retains the configuration that the antigen would have in the absence of the fixative and in other embodiments, a "fixed" antigen has a configuration that is different from the configuration that the antigen would have in the absence of the fixative.

In some embodiments, a fixative of this invention can act by denaturing, precipitating and/or cross-linking proteins in a biological sample. For the purposes of this invention, the process of fixation is understood to generally refer to stabilizing a protein, membrane and/or cell in a natural three-dimensional configuration, as compared to e.g., detergent denaturation, which linearizes a protein.

Nonlimiting examples of fixatives that can be used with the present invention include ethanol, (e.g., 10%, 20%, 30%, 40%, 50% 60%, 70%, 75%, 80%, 85%, 90%, 95% or 100% ethanol), methanol (e.g., 10%, 20%, 30%, 40%, 50% 60%, 70%, 75%, 80%, 85%, 90%, 95% or 100% ethanol), acetone; aldehydes and other cross-linking fixatives including but not limited to formaldehyde, paraformaldehyde, formalin; zinc formalin, glutaraldehyde; acrolein (acrylic aldehyde); glyoxal (ethanedial, diformyl), malonaldehyde (malonic dialdehyde), diacetyl (2,3-butanedione) and the polyaldehydes; metallic ions and oxidizing agents including, but not limited to, osmium tetroxide and chromic acid (chromium trioxide); picric acid; mercuric chloride; Carnoy's fluid (ethanol, chloroform, acetic acid); and zinc acetate and zinc chloride in Tris-Ca buffer; PRESERVCYT® solution (THINPREP® Pap test preparation (Cytic, MA)); BIOFIX® solution (Accra); CYTORICH® fixative system and SUREPATH® fixative (formerly AUTOCYTE® prep) (Tripath Imaging, NC); STRECK CYTOSPRAY® fixative (Streck Laboratories, Omaha Nebr.). The fixative of this invention can be an individual fixative and/or any combination of the fixatives of this invention.

The term "antigen" as used herein, includes any *Trichomonas* antigen that can be contacted with fixative and employed in a method of this invention. A *Trichomonas* antigen of this invention can include, but is not limited to, a whole cell, an isolated protein, a cell fraction, a peptide and/or fragment of a *Trichomonas* protein having antigenic activity. The antigen can also be any protein antigen that is on the surface of a *Trichomonas* organism, any protein antigen that is induced to be placed on the surface of the organism after contact with vaginal epithelial cells during infection, and/or any non-protein structure (e.g., carbohydrate, glycoprotein, lipoprotein, lipid, lipophosphoglycan, etc.) that can serve as an antigen. In some embodiments, a *Trichomonas* antigen of this invention can include, but is not limited to, an antigen of an alpha-actinin protein, an antigen of an adhesin protein, an antigen of phosphoglucomutase, an antigen of glyceraldehyde-3-phosphate dehydrogenase, an antigen with similarity to transcription initiation factor, called TV44, an antigen of enolase and/or an antigen of ferrodoxin oxidoreductase, either individually and/or in any combination. In other embodiments, the antigen of this invention is not an antigen of an alpha-actinin protein, an antigen of an adhesin protein, an antigen of phosphoglucomutase, an antigen of glyceraldehyde-3-phosphate dehydrogenase, an antigen with similarity to transcription initiation factor, called TV44, an antigen of enolase and/or an antigen of ferrodoxin oxidoreductase, either individually and/or in any combination.

An antigen of this invention can also be a *Trichomonas* antigen that remains on any membrane material after filtration of the fixative solution. Membrane material can include fixed whole organisms, membrane components, and/or individual proteins.

The term "antibody" as used herein, includes, but is not limited to, a polypeptide encoded by an immunoglobulin gene or immunoglobulin genes, or fragments thereof. "Antibody" also includes, but is not limited to, a polypeptide encoded by an immunoglobulin gene or immunoglobulin genes, or fragments thereof, which specifically binds to and recognizes the antigen-specific binding region (idiotype) of an antibody produced in response to exposure to fixed *Trichomonas* antigen(s).

An antibody of this invention can be a monoclonal antibody or a polyclonal antibody. An antibody of this invention can be an antibody that specifically binds a *Trichomonas* antigen that has been contacted with a fixative of this invention. In a particular embodiment of this invention, the antibody of this invention binds a *Trichomonas* antigen that has been contacted with fixative(s) used in a Pap smear preparation (e.g., a THINPREP Pap Test preparation).

In some embodiments of this invention, an antibody of this invention is an antibody that specifically binds a fixed *Trichomonas* antigen. For example, an antibody of this invention can be an antibody that specifically binds an antigen of an alpha-actinin protein, an antibody that specifically binds an antigen of an adhesin protein, an antibody that specifically binds an antigen of phosphoglucomutase, an antibody that specifically binds an antigen of glyceraldehyde-3-phosphate dehydrogenase, an antibody that specifically binds an antigen (called TV44, which is recognized by mAb 6B8) with similarity to a transcription initiation factor, an antibody that specifically binds an antigen of enolase and/or an antibody that specifically binds an antigen of ferrodoxin oxidoreductase, either individually and/or in any combination. In other embodiments, the antibody of this invention is not an antibody that specifically binds an antigen of an alpha-actinin protein, an antibody that specifically binds an antigen of an adhesin protein, an antibody that specifically binds an antigen of phosphoglucomutase, an antibody that specifically binds an antigen of glyceraldehyde-3-phosphate dehydrogenase, an antibody that specifically binds an antigen with similarity to transcription initiation factor, called TV44, an antibody that specifically binds an antigen of enolase and/or an antibody that specifically binds an antigen of ferrodoxin oxidoreductase, either individually and/or in any combination.

Nonlimiting examples of monoclonal antibodies that specifically bind fixed Trichonionas antigens and that can be used in the compositions and methods of the present invention include, but are not limited to one or more of the antibodies designated 2C5, 14F8, 14F12, 2C1, 2E10, 8G1, 1A9, 6B8, 12G6 (e.g., 12G6-1, 12G6-2), 9H1, 13C6, 4A10 (e.g., 4A10-1, 4A10-2, 4A10-3), HA423, C55, DM116, 1F12, 11E10, 14B5, 1A4, 6B7-4, 1D4, 13G5, B70, 1F3, 6A12, DM-155, 14G3, 9G12-5, 3B8, 13B8, 9E12, B44-3, SF2, DM-92, 14H6, SF5-15, B66-1, 2H7, 5A2, 9B1, 13F3, DM-9, 1D4, 7H0-7 and B1C20. These antibodies can be employed in the methods of this invention individually and/or in any combination. Furthermore, the compositions and methods of this invention can exclude one or more of the antibodies designated 2C5, 14F8, 14F12, 2C1, 2E10, 8G1, 1A9, 6B8, 12G6-1, 12G6-2, 9H1, 13C6, 4A10-1, 4A10-2, 4A10-3, HA423, C55, DM116, 1F12, 11E10, 14B5, IA4, 6B7-4, 1D4, 13G5, B70, 1F3, 6A12, DM-155, 14G3, 9G12-5, 3B8, 13B8, 9E12, B44-3, SF2, DM-92, 14H6, SF5-15, B66-1, 2H7, 5A2, 9B1, 13F3, DM-9, 1D4, 7H0-7 and B1C20, either individually and/or in any combination.

The term "epitope" as used herein means an antigenic determinant that is specifically bound by an antibody. Epitopes usually consist of surface groupings of molecules such as amino acids (e.g., 6-12 amino acids) and/or sugar side chains and usually have specific three-dimensional structural characteristics, as well as specific charge characteristics. Epitopes can also be conformational in nature, in which case an antibody can interact with distinct regions of proteins (or molecules) that do not make up a contiguous amino acid sequence. In some embodiments, such epitopes may be more readily detected by antibodies generated to fixed antigens.

The terms "specifically binds to" and "specifically reactive with" refer to a binding reaction that is determinative of the presence of the antigen and antibody in the presence of a heterogeneous population of proteins and other biologics. Thus, under designated assay conditions, the specified antibodies and antigens bind to one another and do not bind in a significant amount to other components present in a sample. Specific binding to a target analyte under such conditions may require a binding moiety that is selected for its specificity for a particular target analyte. A variety of immunoassay formats may be used to select antibodies specifically reactive with a particular antigen. For example, solid-phase ELISA immunoassays are routinely used to select monoclonal antibodies specifically immunoreactive with an analyte. See Harlow and Lane (ANTIBODIES: A LABORATORY MANUAL, Cold Springs Harbor Publications, N.Y., (1988)) for a description of immunoassay formats and conditions that can be used to determine specific immunoreactivity. Typically a specific or selective reaction will be at least twice background signal to noise and more typically be more than 10 to 100 times greater than background.

An "immunologically reactive fragment" of a protein refers to a portion of the protein or peptide that is immunologically reactive with a binding partner, e.g., an antibody, which is immunologically reactive with the protein itself.

Antibodies to fixed Trichomonas antigens and/or proteins can be generated using methods that are well known in the art. Such antibodies can include, but are not limited to, polyclonal, monoclonal, chimeric, humanized, single chain, Fab fragments, and fragments produced by an expression library, including phage display. (See, e.g., Paul, FUNDAMENTAL IMMUNOLOGY, 3rd Ed., 1993, Raven Press, New York, for antibody structure and terminology.)

Antibody fragments that contain specific binding sites for a fixed Trichomonas protein can also be generated. For example, such fragments include, but are not limited to, the $F(ab')_2$ fragments that can be produced by pepsin digestion of the antibody molecule, and the Fab fragments that can be generated by reducing the disulfide bridges of the $F(ab')_2$ fragments. Alternatively, Fab expression libraries can be constructed to allow rapid and easy identification of monoclonal Fab fragments with the desired specificity (Huse et al., Science 254, 1275-1281 (1989)).

For the production of antibodies, various hosts including goats, rabbits, rats, mice, humans, and others, may be immunized by injection with a Trichomonas antigen that has been first exposed to fixative or any fragment or oligopeptide or conjugate thereof that has immunogenic properties. Depending on the host species, various adjuvants can be used to increase the immunological response. Such adjuvants include, but are not limited to, Freund's complete and incomplete adjuvant, mineral gels such as aluminum hydroxide, and surface active substances such as lysolecithin, pluronic polyols, polyanions, peptides, oil emulsions, keyhole limpet hemocyanin, and dinitrophenol. Examples of adjuvants used in humans include BCG (bacilli Calmette-Guerin) and Corynebacterium parvum.

Monoclonal antibodies to Trichomonas proteins can be prepared using any technique that provides for the production of antibody molecules by continuous cell lines in culture. These include, but are not limited to, the hybridoma technique, the human B-cell hybridoma technique, and the EBV-hybridoma technique (Kohler et al. (1975) Nature 256:495-497; Kozbor et al. (1985) J. Immunol. Methods 81:31-42; Cote et al. (1983) Proc. Natl. Acad. Sci. 80:2026-2030; Cole et al. (1984) Mol. Cell BioL 62:109-120).

In one embodiment, the present invention provides methods of producing a monoclonal antibody, comprising the steps of (a) immunizing an animal with a antigen from Trichomonas that has been contacted with a fixative; (b) obtaining cells that produce antibodies specific for fixed Trichomonas antigens; (c) fusing the cells with a myeloma cell line to create hybridomas secreting the antibodies; (d) screening the hybridomas; and (e) selecting the hybridomas producing antibodies that specifically bind to fixed antigens from Trichomonas.

In some embodiments, the antigen which is used for immunizing an animal is a fixed Trichomonas cell. In other embodiments, the animal is immunized with a fixed Trichomonas protein or immunogenic fragment or oligopeptide or conjugate thereof. For example, haptenic oligopeptides of a fixed

*Trichomonas* protein can be conjugated to a carrier protein to be used as an immunogen. Lymphoid cells (e.g., splenic lymphocytes) are then obtained from the immunized animal and fused with immortalizing cells (e.g., myeloma or heteromyeloma) to produce hybrid cells. The hybrid cells are screened to identify those that produce the desired antibody.

Human hybridomas that secrete human antibody can be produced by the Kohler and Milstein technique. Although human antibodies are especially preferred for treatment of humans, in general, the generation of stable human-human hybridomas for long-term production of human monoclonal antibody can be difficult. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See Oi et al., *Bio Techniques* 4(4):214-221 (1986); Sun et al., *Hybridoma* 5 (1986).

The monoclonal antibodies of this invention specific for fixed *Trichomonas* protein epitopes can also be used to produce anti-idiotypic (paratope-specific) antibodies. (See e.g., McNamara et al., *Science* 220, 1325-26 (1984); Kennedy et al., *Science* 232:220 (1986).) These antibodies resemble the fixed *Trichomonas* protein epitope and thus, can be used as an antigen to stimulate an immune response against the fixed *Trichomonas* protein.

In addition, techniques developed for the production of "chimeric antibodies," the splicing of mouse antibody genes to human antibody genes to obtain a molecule with appropriate antigen specificity and biological activity can be used (Morrison et al. *Proc. Natl. Acad. Sci.* 81:6851-6855 (1984); Neuberger et al., *Nature* 312:604-608 (1984); Takeda et al., *Nature* 314:452-454 (1985)). Alternatively, techniques described for the production of single chain antibodies can be adapted, using methods known in the art, to produce *Trichomonas* protein-specific single chain antibodies. Antibodies with related specificity, but of distinct idiotypic composition, can be generated by chain shuffling from random combinatorial immunoglobin libraries (Burton, *Proc. Natl. Acad. Sci.* 88:11120-3 (1991)).

Antibodies can also be produced by inducing in vivo production in the lymphocyte population or by screening immunoglobulin libraries or panels of highly specific binding reagents as described in the literature (Orlandi et al., *Proc. Natl. Acad. Sci.* 86:3833-3837 (1989)); Winter et al., *Nature* 349:293-299 (1991)).

Various immunoassays can be used to identify antibodies of this invention having the desired specificity. Furthermore, a wide variety of immunoassays may be employed in the methods of this invention to detect antibodies and antigens of fixed *Trichomonas* proteins for diagnosis of *Trichomonas* infection. Such immunoassays typically involve the measurement of antigen/antibody complex formation between a fixed *Trichomonas* protein or peptide and its specific antibody.

Thus, a further embodiment of the present invention provides a method of identifying an antibody that binds a fixed *Trichomonas* antigen, comprising: a) contacting the antibody with a fixed *Trichomonas* antigen under conditions whereby an antigen/antibody complex can form; and b) detecting formation of an antigen/antibody complex, thereby identifying an antibody that binds a fixed *Trichomonas* antigen. Such an antibody can be further evaluated for the ability to bind a *Trichomonas* antigen that has not been contacted with a fixative according to the immunoassays of this invention, resulting in the identification of an antibody that binds a fixed *Trichomonas* antigen and does not bind a *Trichomonas* antigen that has not been contacted with a fixative. In some embodiments, an antibody of this invention can be an antibody that binds a fixed *Trichomonas* antigen and does not bind a *Trichomonas* antigen that has not been contacted with a fixative and in other embodiments, an antibody of this invention can be an antibody that binds a fixed *Trichomonas* antigen and also binds a *Trichomonas* antigen that has not been contacted with a fixative. Such an antibody can be, for example, a monoclonal antibody produced by a hybridoma cell or an antibody present in a polyclonal population of antibodies, e.g., in a biological sample.

The immunoassays of the invention can be either competitive or noncompetitive. In competitive binding assays, fixed *Trichomonas* antigen or antibody competes with a detectably labeled fixed *Trichomonas* antigen or antibody for specific binding to a capture site bound to a solid surface. The concentration of labeled antigen or antibody bound to the capture agent is inversely proportional to the amount of free antigen or antibody present in the sample.

Noncompetitive assays can be, for example, sandwich assays, in which the sample analyte (target antibody) is bound between two analyte-specific binding reagents. One of the binding agents is used as a capture agent and is bound to a solid surface. The other binding agent is labeled and is used to measure or detect the resultant antigen/antibody complex by e.g., visual or instrument means. A number of combinations of capture agent and labeled binding agent can be used. For instance, fixed antigens derived from the *Trichomonas* can be used as the capture agent and labeled anti-human antibodies specific for the constant region of human antibodies can be used as the labeled binding agent to detect antibodies in a sample that bind the fixed *Trichomonas* antigen. Goat, sheep and other non-human antibodies specific for human immunoglobulin constant regions are well known in the art. Alternatively, the anti-human antibodies can be the capture agent and the antigen can be labeled. Other proteins capable of specifically binding human immunoglobulin constant regions, such as protein A, protein L or protein G can also be used as the capture agent or labeled binding agent. These proteins are normal constituents of the cell walls of streptococcal bacteria. They exhibit a strong nonimmunogenic reactivity with immunoglobulin constant regions from a variety of species. (See, e.g., Kronval et al., *J. Immunol.*, 111:1401-1406 (1973); Akerstrom et al., *J. Immunol.*, 135:2589-2542 (1985)).

The non-competitive assays need not be sandwich assays. For instance, the antibodies or antigens in the sample can be bound directly to the solid surface. The presence of antibodies or antigens in the sample can then be detected using labeled antigen or antibody, respectively.

In some embodiments, antibodies and/or fixed *Trichomonas* proteins can be conjugated or otherwise linked or connected (e.g., covalently or noncovalently) to a solid support (e.g., bead, plate, slide, dish, membrane or well) in accordance with known techniques. Antibodies can also be conjugated or otherwise linked or connected to detectable groups such as radiolabels (e.g., $^{35}$S, $^{125}$I, $^{32}$P, $^{3}$H, $^{14}$C, $^{131}$I), enzyme labels (e.g., horseradish peroxidase, alkaline phosphatase), gold beads, chemiluminescence labels, ligands (e.g., biotin) and/or fluorescence labels (e.g., fluorescein) in accordance with known techniques.

A variety of organic and inorganic polymers, both natural and synthetic can be used as the material for the solid surface. Nonlimiting examples of polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that can be used include, but are not limited to, include paper, glass, ceramic, metal, metalloids, semiconductive materials, cements and the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes can be employed depending upon the nature of the system.

A variety of immunoassay systems can be used, including but not limited to, radio-immunoassays (RIA), enzyme-linked immunosorbent assays (ELISA) assays, enzyme immunoassays (EIA), "sandwich" assays, gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin/avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, etc., immunoprecipitation, competitive binding assays and immunohistochemical staining. These and other assays are described, among other places, in Hampton et al. (*Serological Methods, a Laboratory Manual*, APS Press, St Paul, Minn. (1990)) and Maddox et al. (*J. Exp. Med.* 158:1211-1216 (1993)).

The methods of this invention can also be carried out using a variety of solid phase systems, such as described in U.S. Pat. No. 5,879,881, as well as in a dry strip lateral flow system, such as described, for example, in U.S. Patent Publication No. 20030073147, the entire contents of each of which are incorporated by reference herein.

A subject of this invention is any animal that can be infected by *Trichomonas*. In certain embodiments, the subject is human. In further embodiments of this invention, the subject is a female human.

The antibodies of this invention can be used in in vitro and/or in in situ assays to detect a *Trichomonas* protein or peptide of this invention.

Also as used herein, the terms peptide and polypeptide are used to describe a chain of amino acids, which correspond to those encoded by a nucleic acid. A peptide usually describes a chain of amino acids of from two to about 30 amino acids and polypeptide usually describes a chain of amino acids having more than about 30 amino acids. The term polypeptide can refer to a linear chain of amino acids or it can refer to a chain of amino acids, which have been processed and folded into a functional protein. It is understood, however, that 30 is an arbitrary number with regard to distinguishing peptides and polypeptides and the terms may be used interchangeably for a chain of amino acids around 30. The peptides and polypeptides of the present invention are obtained by isolation and purification of the peptides and polypeptides from cells where they are produced naturally or by expression of a recombinant and/or synthetic nucleic acid encoding the peptide or polypeptide and then exposed to a fixative prior to use in the preparation of antibodies. The peptides and polypeptides of this invention can be obtained by chemical synthesis, by proteolytic cleavage of a polypeptide and/or by synthesis from nucleic acid encoding the peptide or polypeptide.

It is also understood that the peptides and polypeptides of this invention may also contain conservative substitutions where a naturally occurring amino acid is replaced by one having similar properties and which does not alter the function of the peptide or polypeptide. Such conservative substitutions are well known in the art. Thus, it is understood that, where desired, modifications and changes may be made in the nucleic acid and/or amino acid sequence of the peptides and polypeptides of the present invention and still obtain a peptide or polypeptide having like or otherwise desirable characteristics. Such changes may occur in natural isolates or may be synthetically introduced using site-specific mutagenesis, the procedures for which, such as mis-match polymerase chain reaction (PCR), are well known in the art. One of skill in the art will also understand that polypeptides and nucleic acids that contain modified amino acids and nucleotides, respectively (e.g., to increase the half-life and/or the therapeutic efficacy of the molecule), can be used in the methods of the invention.

The present invention further provides a kit for detection of antigens and/or antibodies of this invention. In one embodiment, a kit of this invention can comprise a polypeptide, a peptide, an antigenic fragment and/or a fusion protein or peptide comprising a fixed antigen, along with suitable buffers, wash solutions, dilution buffers, secondary antibodies, detection reagents, etc. for the detection of antigen/antibody complex formation under various conditions. In other embodiments, and/or in combination with the kit described above, a kit of this invention can comprise one or more antibodies of this invention, along with suitable buffers, wash solutions, dilution buffers, secondary antibodies, detection reagents, etc. for the detection of antigen/antibody complex formation under various conditions.

The present invention is more particularly described in the Examples set forth below, which are not intended to be limiting of the embodiments of this invention.

EXAMPLES

Example 1

Generation of Anti-Methanol Fixed *Trichomonas Vaginalis* Monoclonal Antibodies Antigen preparation. Fresh *T. vaginalis* isolate T016 was cultured in 10% heat-inactivated horse serum Trypticase-Yeast-Maltose medium for 18 h. The organisms were harvested by centrifugation and washed 3× with cold PBS. The washed-organisms were suspended in PBS and enumerated before fixation in cold 20% methanol prepared in PBS. The fixed organisms were incubated over-night at 4° C. Finally, the fixed organisms were washed 3× w/ PBS, and resuspended to $1\times10^7$ organisms/ml.

Mouse immunization. Five female Balb/C mice aged 4 weeks were immunized with 0.5 ml of antigen ($5\times10^6$ fixed organisms) and mixed with 0.5 ml Freund's Complete adjuvant for the first immunization and followed by an identical dosage of organisms mixed with Incomplete adjuvant for the booster immunization. Two hundred microliters of material were inoculated into each mouse by subcutaneous injection. Each mouse received the equivalent of $1\times10^6$ fixed organisms. Three other subsequent booster immunizations were given to each mouse at intervals of 14 days. The mice that had the highest antibody titers were used for fusion of lymphocytes with NS/1 myeloma cells.

Fusion, screen and cloning monoclonal antibodies (mAbs). Hybridomas that produced antibody against the fixed proteins (antigens) were selected by using a whole-cell ELISA assay. The ELISA plates were prepared by first coating them with 50 µl of 1×10⁵ organisms per well. The organisms were washed in phosphate buffered saline (PBS). The plates were incubated at 37° C. and air-dried. When the plates were dry, 100 µl/well of 20% methanol was added to fix the organisms. Following evaporation of the methanol, the plates were washed 3 times with PBS to remove any unbound antigen. The ELISA plate wells were blocked for 2 hours at room temperature with 200 µl of 10% skim milk prepared in PBS. Finally, the plates were washed once more with PBS, air-dried and stored at 4° C.

The hybridoma supernatant was screened using an ELISA. One hundred microliters per well of hybridoma supernatant each were loaded into individual wells of ELISA plates and incubated at 37° C. for 2 h. The wells were washed 3 times with 0.05% Tween-20-PBS. One hundred microliters of secondary goat anti mouse immunoglobulins (Igs) (anti-IgA, IgG, and IgM) conjugated to horse radish peroxidase were added to each well and the plates were incubated at 37° C. for 1 hr. Finally, the wells were washed 3 times with 100 µl of 0.05% Tween-20-PBS, followed with 100 µl/well of the substrate, ABTS (2,2'-AZINO bis(3ETHYLBENZTHIAZOLINE-6-SULFONIC ACID) tablets (Sigma A-9941) in solution, and incubated at RT for 20 min. The results were evaluated by an ELISA reader (EL 808, Bio-Tak Instrument. Inc.).

Example 2

Filtration ELISA

A 96 well filter-plate (Corning Cat. NO. 3510, 0.25 mm Glass Fiber/1.2 µm PES membrane 96 well filter plate) was used for the suspended, fixed whole organism ELISA. First, a fresh $T.$ $vaginalis$ (T016) culture was harvested and washed 3 times with cold PBS. The washed-organisms were fixed in PRESERVCYT® solution (Pap smear sample fixation buffer, Cytyc Corporation, 85 Swanson Rd, Boxborough, Mass. 01719). The fixed organisms were incubated over-night at 4° C. Finally, the fixed organisms were counted and adjusted to a density of 1×10⁶ organisms/ml of organisms in the same solution. These suspended organisms are used as the antigen for a filtration ELISA.

For the ELISA procedure, the wells are first pre-wet and blocked with 100 µl of 1% BSA in 0.05% Tween 20/PBS for five minutes at room temperature, then the plate is placed on the vacuum base with a plate holder to remove the buffer by vacuum (vacuum-flow-through washing method). Next, 100 µl of suspended fixed antigen, 1×10⁵ organisms/well (for the ABTS substrate) or 1×10⁴ organisms/well (for the ECL substrate) is added to the filter plate. The fixative present in the antigen preparation is removed by vacuum filtration. One hundred microliters of 1% Triton X-100/PBS is then added into each well and the plate is incubated at room temperature for 10 minutes. Following incubation, the Triton X-100/PBS is removed and the antigen is washed 3 times with 200 µl/well of 0.05% Tween 20/PBS using the vacuum-flow-through washing method. One hundred microliters of mAb are added to each well and the plate is incubated at room temperature for 15 min. The mAb is removed and the wells are washed 3 times with 200 µl of PBS Tween-20. The waste PBS is removed using the vacuum-flow-through washing method.

One hundred microliters of secondary Abs (anti-mouse IgG, IgM, IgA HRP conjugated) are added into each well and the plates are incubated at room temperature for 15 min. The secondary antibodies are removed and the wells are washed 3 times with 200 µl of PBS Tween-20. The waste PBS is removed using the vacuum-flow-through washing method.

Then, 100 µl color substrate solution is added into each well and the plates are incubated at room temperature for 20 min. The color is read directly or the developed color solution is first transferred to a new 96 well culture plate and then the new plate containing the transferred solution is read using an ELISA reader. For the ECL assay, 20 µl of ECL substrate is added. The plates are incubated at room temperature for 5 min (covered w/ aluminum fold to prevent exposure to light) and then exposed using ECL film (with 0.5 second). Finally, either the film can be developed or the plate can be read using an ECL-ELISA reader.

Example 3

Rapid Flow-Through Immunofiltration Assay System for Rapid Detection of $Trichomonas$ $Vaginalis$ in Thinprep® Pap Test Preparation Specimens The present invention provides a rapid flow-through filtration assay system to detect $T.$ $vaginalis$ in THINPREP® Pap test preparation specimens.

Methods. Spleen lymphocytes of mice immunized with trichomonads from fresh $T.$ $vaginalis$ culture after treatment with THINPREP® (TP) Pap test preparation were fused with NS1 myeloma cells to generate hybridomas producing mAbs. Supernatants of hybridomas were tested for reactivity with organisms from fresh $T.$ $vaginalis$ culture exposed to THINPREP® fixative coating microtiter wells. Immunoreactive mAbs of single cell-cloned hybridomas were tested for detection of trichomonad antigen in THINPREP® Pap test preparation fixed specimens under optimized conditions. The mAbs were examined using a Filtration assay system on disposable porous filter-membranes with bound antigen. Finally, THINPREP® Pap test preparation fixed specimens from patients with trichomonosis and uninfected individuals were tested for reactivity by mAbs using the Filtration assay.

Monoclonal antibodies were identified by standard colorimetric ELISA at 405 nm that immunoreacted with trichomonads exposed to THINPREP® Pap test preparation coated onto microtiter wells. The mAbs detected fixed trichomonad antigen immobilized onto membranes in a Filtration assay system. Both colorimetric ELISA and emission chemiluminescence (ECL) assays were used. The Filtration ECL assay was very sensitive and detected antigen from as little as 10 organisms immobilized on membranes. Filtration ECL yielded rapid, accurate results with fewer fixed organisms within 30 sec compared to colorimetric ELISA. The mAbs reacted with organisms added to the THINPREP® Pap test preparation and with antigen in samples of patients with trichomonosis. No immuno-crossreactivity was detected with the mAbs with other trichomonad species, in the absence of the fixed $T.$ $vaginalis$ antigen, and in samples with materials from uninfected individuals. Thus, the present invention provides to detect $Trichomonas$ in the liquid-based THINPREP® Pap test preparation specimens in a sensitive and specific manner.

Example 4

Detection of Fixed $Trichomonas$ Antigens by Monoclonal Antibodies Prepared using Fixed $Trichomonas$ Organisms Patient samples prepared according to the THINPREP® Pap test preparation method were exposed to the antibodies of the present invention. The results are shown in Table 2.

Various monoclonal antibodies were prepared according to method of the present invention and their absorbance readings in a colorimetric ELISA measuring reactivity to fixed *Trichomonas* antigen (100,000 organisms per well) were determined. Many of these monoclonal antibodies were shown to work in a specific and sensitive manner, including 12G6, 2C5, 9H1, 13C6, 14F8 and 14F12. The identity of some of the antigens that are bound by the mAbs has been determined. For example, the mAb HA423 (deposited under Accession No. PTA-10802 on May 4, 2010 with the American Type Culture Collection, University Boulevard, Manassas, Va., 20110-2209), is IgG1 and reactive to alpha-actinin, the mAbs 9H1 and 136C are reactive with a protein of approximately 38 kDa molecular weight, which is believed to be glyceraldeyde-3-phosphate dehydrogenase (GAPDH), the mAb 14F8 is reactive with a protein of approximately 15-20 kDa molecular weight and the mAb 14F12 is reactive with a protein of approximately 65 kDa molecular weight.

Example 5

Relationship of the Number of *Trichomonas* Organisms to the Response of the Monoclonal Antibodies in a Colorimetric ELISA The relationship of the number of *Trichomonas* organisms present to the response of the monoclonal antibodies (mAbs) of the present invention in a colorimetric ELISA is shown in Table 1.

TABLE 1

| | mAb: | | | | |
|---|---|---|---|---|---|
| Number of Fixed *T. vaginalis* cells | NS1 ELISA O.D. | C55 ELISA O.D. | 2C5 ELISA O.D. | 14F8 ELISA O.D. | 14F12 ELISA O.D. |
| $1 \times 10^5$ | 0.000 | 0.129 | 0.409 | 0.270 | 0.706 |
| $1 \times 10^4$ | 0.000 | 0.023 | 0.157 | 0.083 | 0.271 |
| $1 \times 10^3$ | 0.000 | 0.007 | 0.027 | 0.063 | 0.072 |
| $1 \times 10^2$ | 0.000 | 0.000 | 0.005 | 0.066 | 0.029 |

Example 6

Filtration Assay of Specimens from Patients

Patient samples prepared according to the THINPREP® method were exposed to the antibodies of the present invention. The results are shown in Table 2.

TABLE 2

| mAb: Patient Pap Smear Sample | 2C5 ELISA O.D. | 14F8 ELISA O.D. | 14F12 ELISA O.D. |
|---|---|---|---|
| 1 | 0.186 | 0.166 | 0.230 |
| 2 | 0.069 | 0.126 | 0.139 |
| 3 | 0.086 | 0.147 | 0.138 |
| 4 | 0.126 | 0.161 | 0.212 |

Each of the mAbs tested was able to detect the *Trichomonas* organisms present in the Pap smear samples.

Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference into this application in order to more fully describe the state of the art to which this invention pertains.

What is claimed is:

1. A method of detecting a *Trichomonas* antigen in a sample from a human subject, wherein the sample from the subject has been contacted with fixative, comprising: a) contacting the sample with an antibody that specifically binds a fixed *Trichomonas* alpha actinin antigen under conditions whereby an antigen/antibody complex can form; and b) detecting the formation of an antigen/antibody complex, thereby detecting the *Trichomonas* antigen in the sample, wherein the antibody is a monoclonal antibody produced from the hybridoma cell line HA423, deposited with the American Type Culture Collection under Accession No. PTA-10802.

2. A method of detecting a *Trichomonas* antigen in a sample from a human subject, comprising: a) contacting the sample from the subject with a fixative; b) contacting the sample of (a) with an antibody that specifically binds a fixed *Trichomonas* alpha actinin antigen under conditions whereby an antigen/antibody complex can form; and c) detecting the formation of an antigen/antibody complex, thereby detecting the *Trichomonas* antigen in the sample, wherein the antibody is a monoclonal antibody produced from the hybridoma cell line HA423, deposited with the American Type Culture Collection under Accession No. PTA-10802.

3. A method of diagnosing *Trichomonas* infection in a human subject, comprising: a) contacting a sample from the subject, wherein the sample has been contacted with a fixative, with an antibody that specifically binds a fixed *Trichomonas* alpha actinin antigen under conditions whereby an antigen/antibody complex can form; and b) detecting formation of an antigen/antibody complex, thereby diagnosing a *Trichomonas* infection in the subject, wherein the antibody is a monoclonal antibody produced from the hybridoma cell line HA423, deposited with the American Type Culture Collection under Accession No. PTA-10802.

4. A method of diagnosing *Trichomonas* infection in a human subject, comprising: a) contacting a sample from the subject with a fixative; b) contacting the sample of (a) with an antibody that specifically binds a fixed *Trichomonas* alpha actinin antigen under conditions whereby an antigen/antibody complex can form; and c) detecting formation of an antigen/antibody complex, thereby diagnosing *Trichomonas* infection in the subject, wherein the antibody is a monoclonal antibody produced from the hybridoma cell line HA423, deposited with the American Type Culture Collection under Accession No. PTA-10802.

5. The method of claim 1, wherein the sample is a Pap smear preparation.

6. The method of claim 1, wherein the fixative is selected from the group consisting of ethanol, methanol, acetone, formaldehyde, paraformaldehyde, formalin, glutaraldehyde, osmium tetroxide, chromic acid and any combination thereof.

7. The method of claim 2, wherein the sample is a Pap smear preparation.

8. The method of claim 2, wherein the fixative is selected from the group consisting of ethanol, methanol, acetone, formaldehyde, paraformaldehyde, formalin, glutaraldehyde, osmium tetroxide, chromic acid and any combination thereof.

9. The method of claim 3, wherein the sample is a Pap smear preparation.

10. The method of claim 3, wherein the fixative is selected from the group consisting of ethanol, methanol, acetone, formaldehyde, paraformaldehyde, formalin, glutaraldehyde, osmium tetroxide, chromic acid and any combination thereof.

11. The method of claim 4, wherein the sample is a Pap smear preparation.

12. The method of claim 4, wherein the fixative is selected from the group consisting of ethanol, methanol, acetone, formaldehyde, paraformaldehyde, formalin, glutaraldehyde, osmium tetroxide, chromic acid and any combination thereof.

* * * * *

UNITED STATES PATENT AND TRADEMARK OFFICE
CERTIFICATE OF CORRECTION

PATENT NO. : 7,803,567 B2
APPLICATION NO. : 11/634766
DATED : September 28, 2010
INVENTOR(S) : Alderete et al.

It is certified that error appears in the above-identified patent and that said Letters Patent is hereby corrected as shown below:

On Title Page:
Item (56), References Cited, Other Publications, Page 3, left column,
 line 5 "Van der Schee et al.":
 Please correct "of iTrichomonas" to read -- of Trichomonas --

In the Specification:
Column 12, Example 4, Lines 65-67:
 Please delete paragraph: "Patient samples prepared according to the
 THINPREP® Pap test preparation method were exposed to the antibodies
 of the present invention. The results are shown in Table 2."

Column 13, Line 11: Please correct "Collection, University"
 to read -- Collection, 10801 University --
 Lines 47-48: Please correct "THINPREP® method"
 to read -- THINPREP® Pap test preparation method --

Signed and Sealed this
Twenty-sixth Day of April, 2011

David J. Kappos
*Director of the United States Patent and Trademark Office*